United States Patent [19]
Guddal et al.

[11] Patent Number: 5,830,757
[45] Date of Patent: Nov. 3, 1998

[54] STIMULATION OF MEIOSIS

[75] Inventors: Erling Guddal, Brøndby; Anne Grete Byskov, Gentofte; Frederik Christian Grønvald, Vebæk; Lars Nordholm, Herlev, all of Denmark

[73] Assignee: Novo Nordisk A/S, Bagsvaerd, Denmark

[21] Appl. No.: 807,928

[22] Filed: Feb. 28, 1997

Related U.S. Application Data

[63] Continuation of Ser. No. 448,214, May 23, 1995, abandoned.

[30] Foreign Application Priority Data

Mar. 6, 1995 [DK] Denmark ................... 0232/95
Mar. 24, 1995 [DK] Denmark ................... 0309/95

[51] Int. Cl.⁶ ............... C12N 5/00; C12N 9/02; C12N 9/90
[52] U.S. Cl. ............ 435/325; 435/183; 435/189; 435/233; 435/52
[58] Field of Search ................ 435/325, 183, 435/189, 233, 52

*Primary Examiner*—Leon B. Lankford, Jr.
*Attorney, Agent, or Firm*—Steve T. Zelson, Esq.; Valeta A. Gregg, Esq.

[57] ABSTRACT

The present invention relates to the use of certain chemical compounds which interfere with the biosynthesis of cholesterol and medicaments comprising such compounds for stimulating the meiosis of oocytes and spermatozoon in vivo, ex vivo and in vitro.

8 Claims, No Drawings

STIMULATION OF MEIOSIS

This application is continuation of application Ser. No. 08/448,214 filed May 23, 1995, now abandoned, and claims priority to Danish application Ser. No. 0232/95 filed on Mar. 6, 1995 in Denmark and application Ser. No. 0309/95 filed on Mar. 24, 1995 in Denmark, the contents of which applications are fully incorporated herein by reference in their entirety.

FIELD OF THE INVENTION

The present invention relates to a method of inducing meiosis in a germ cell and to the use of certain chemical compounds and medicaments comprising such compounds for stimulating the meiosis in vivo, ex vivo and in vitro.

BACKGROUND OF THE INVENTION

Meiosis is the unique and ultimate event of germ cells on which sexual reproduction is based. Meiosis comprises two meiotic divisions. During the first division, exchange between maternal and paternal genes takes place before the pairs of chromosomes are separated into the two daughter cells. These contain only half the number (1n) of chromosomes and 2c DNA. The second meiotic division proceeds without a DNA synthesis. This division therefore results in the formation of the haploid germ cells with only 1c DNA.

The meiotic events are similar in the male and female germ cells, but the time schedule and the differentiation processes which lead to ova and to spermatozoa differ profoundly. All female germ cells enter the prophase of the first meiotic division early in life, often before birth, but all are arrested as oocytes later in the prophase (dictyate state) until ovulation after puberty. Thus, from early life the female has a stock of oocytes which is drawn upon until the stock is exhausted. Meiosis in females is not completed until after fertilization, and results in only one ovum and two abortive polar bodies per germ cell. In contrast, only some of the male germ cells enter meiosis from puberty and leave a stem population of germ cells throughout life. Once initiated, meiosis in the male cell proceeds without significant delay and produces 4 spermatozoa.

Only little is known about the mechanisms which control the initiation of meiosis in the male and in the female. In the oocyte, new studies indicate that follicular purines, hypoxanthine or adenosine, could be responsible for meiotic arrest (Downs et al., *Dev. Biol.* 82, pp. 454–458 (1985); Eppig et al. *Dev. Biol.* 119, pp. 313–321 (1986); and Downs, *Mol. Reprod. Dev.* 35, pp. 82–94 (1993)). The presence of a diffusible meiosis regulating substance was first described by Byskov et al. in a culture system of fetal mouse gonads (Byskov et al. *Dev. Biol.* 52, pp. 193–200 (1976)). A meiosis activating substance (MAS) was secreted by the fetal mouse ovary in which meiosis was ongoing, and a meiosis preventing substance (MPS) was released from the morphologically differentiated testis with resting, non-meiotic germ cells. It was suggested that the relative concentrations of MAS and MPS regulated the beginning, arrest and resumption of meiosis in the male and in the female germ cells (Byskov et al. in The Physiology of Reproduction (eds. Knobil, E. and Neill, J. D., Raven Press, New York (1994)). Clearly, if meiosis can be regulated, reproduction can be controlled. Thus, if stimulation of the meiosis of an oocyte is desired, one conceivable way of achieving this is to secure that the amount of MAS present in the environment of the oocyte outweighs the amount of MPS present. This could, in principle, be done by administering a MAS, by stimulating the secretion of a MAS or by blocking the biotransformation of a MAS already present.

SUMMARY OF THE INVENTION

It has earlier been found that administration of certain sterols known as intermediates in the biosynthesis of cholesterol leads to stimulation of the meiosis. Surprisingly, it has now turned out that administration of certain compounds, known to interfere with the biosynthesis of cholesterol, can also lead to a stimulation of the meiosis.

Accordingly, in its broadest aspect, the present invention relates to a method of stimulating the meiosis of a germ cell which comprises administering to said cell in vivo, ex vivo or in vitro an effective amount of a compound which causes accumulation of an endogenous meiosis activating substance to a level at which meiosis is induced.

According to a preferred embodiment, the present invention relates to a method of stimulating the meiosis of a mammalian germ cell.

According to another preferred embodiment, the present invention relates to a method of stimulating the meiosis of a human germ cell.

According to another preferred embodiment, the present invention relates to a method of stimulating the meiosis of an oocyte.

According to another preferred embodiment, the present invention relates to a method of stimulating the meiosis of a spermatozoon.

According to another preferred embodiment, the present invention relates to a contraceptive method for use in females.

According to another preferred embodiment, the present invention relates to a method of treating infertility by stimulating the formation of meiotic oocytes so that an increased number of meiotic oocytes are available when the ovulatory peak of gonadotropins occurs.

According to another preferred embodiment, the present invention relates to a method of treating infertility in males by stimulating the formation of spermatozoon from male germ cells.

According to another preferred embodiment, the present invention relates to a method of stimulating the meiosis of a germ cell which comprises administering a compound which exhibits meiosis activating properties when tested according to at least one of the methods described in the examples of the present specification.

According to another preferred embodiment, the present invention relates to a method of stimulating the meiosis of a germ cell which comprises administering a compound selected from the group comprising amphotericin B, aminoguanidine and 3β,5α,6β-trihydroxycholestane.

According to another preferred embodiment, the present invention relates to the use of a compound which causes accumulation of an endogenous meiosis activating substance to a level at which meiosis is induced for the preparation of a medicament for inducing meiosis.

According to another preferred embodiment, the present invention relates to the use of a compound which exhibits meiosis activating properties when tested according to at least one of the methods described in the examples of the present specification for the preparation of a medicament for inducing meiosis.

According to a further preferred embodiment, the present invention relates to the use of a compound which causes accumulation of an endogenous meiosis activating substance to a level at which meiosis is induced which compound is selected from the group comprising amphotericin B, aminoguanidine and 3β,5α,6β-trihydroxycholestane for the preparation of a medicament for inducing meiosis.

DETAILED DESCRIPTION OF THE INVENTION

The existence of a meiosis activating or stimulating substance has been known for some time. However, until recently, the identity of the meiosis activating substance or substances was unknown.

The prospects of being able to influence the meiosis are several. According to a preferred embodiment of the present invention, the selected compounds are used to stimulate the meiosis. According to another preferred embodiment of the present invention, the selected compounds are used to stimulate the meiosis in humans. Thus, the selected compounds are promising as fertility regulating agents. It can be expected that the usual side effect on the somatic cells which are known from the hitherto used hormonal contraceptives which are based on estrogens and/or gestagens will not be found with the present invention. For use as a contraceptive agent in females, meiosis can be induced so as to prematurely induce resumption of meiosis in oocytes while they are still in the growing follicle, before the ovulatory peak of gonadotropins occurs. In women, the resumption of the meiosis can, for example, be induced a week after the preceding menstruation has ceased. When ovulated, the resulting overmature oocytes are most likely not to be fertilized. The normal menstrual cycle is not likely to be affected. In this connection, it is important to notice that the progesterone synthesis in cultured human granulosa cells (somatic cells of the follicle) is not affected by the presence of a meiosis inducing substance, whereas the estrogens and gestagens used in the hitherto used hormonal contraceptives do have an adverse effect on the progesterone synthesis.

Stimulation of meiosis in male germ cells has also been demonstrated. Accordingly, the present invention may also be useful for the treatment of infertility in males.

Lanosta-8,24-diene-3β-ol (lanosterol) which is devoid of any meiosis activating properties is the primary cyclization product in the sterol synthesis in mammalian cells. The subsequent biosynthesis of cholesterol proceeds through a series of steps like demethylations, oxidations, reductions and displacements of double bonds, all of which are enzymatically controlled. Only some of the enzymes controlling these steps have been isolated and characterized. The first product formed with a cholestane skeleton is 4,4dimethylcholesta-8,14,24-triene-3β-ol, which is identical with a meiosis activating compound isolated from human follicle fluid (A G Byskov et al. Nature, in press). Subsequent reduction of the double bond in the 14-position produces 4,4-dimethylcholesta-8,24-diene-3β-ol, which is identical with a meiosis activating compound isolated from bull testes (A G Byskov et al. Nature, in press). Stepwise removal of the methyl groups in the 4-position produces 4-methylcholesta-8,24-diene-3β-ol and cholesta-8,24-diene-3β-ol (zymosterol) both of which have meiosis activating properties. Subsequent migration of the double bond from the 8-position to the 5-position produces cholest-5-ene-3β-ol (cholesterol) which has no meiosis activating properties. Inhibition of any of the enzymes which are active in the series of reactions described above will cause upstream intermediates with meiosis activating properties to accumulate, thereby inducing meiosis in germ cells present.

A number of compounds known from literature have been described as inhibitors for one or more of the enzymes involved in the in vivo conversion of lanosta-8,24-diene-3β-ol to cholesterol and the field has recently been reviewed (Mercer, *Pros. Lipid Res.* 32, pp. 357–416 (1993)). Amphotericin is known to interfere with the late steps of the ergosterol synthesis in fungi (Coulon et al. *Can. J. Microbiol.* 32, pp. 738–42 (1986)) and is used in the clinic as an antimycotic. In rat liver in vitro, cholestantriol has been found to interfere with the demethylation in the 4-position of intermediates in the biosynthesis of cholesterol and thus induce accumulation of 4,4-dimethylcholesta-8-ene-3-ol and 4-methylcholesta-8-ene-3-ol (Scallen et al., *J. Biol. Chem.* 246, pp. 3168–74 (1971)).

The amount to be administered of the active agent of this invention is determined according to the purpose of the treatment by those skilled in the art. The amount will depend i.a on the specific agent in question, on the particular mode of administration (e.g. in vivo, ex vivo or in vitro) and on other factors.

Compositions according to the invention for administering the active agents may be in the form of tablets, capsules, powders, solutions or suspensions. In such compositions, the active agents may be combined with the carriers, adjuvants, and vehicles usually employed in the art.

A systemic effect can be achieved by oral administration or by injection or infusion of sterile solutions of the active agents according to the invention, the solutions being prepared according to the known art. Also, a systemic effect can be achieved by inhalation or by nasal administration of a powder or an aerosol containing the active agent.

The present invention is further illustrated by the following examples which, however, are not to be construed as limiting the scope of protection. The features disclosed in the foregoing description and in the following examples may, either separately or in any combination thereof, be material for realizing the invention in diverse forms thereof.

EXAMPLES

Materials and Methods

Test of meiosis activating substances in the oocyte test.

Animals

Immature female mice (B6D2-F1, strain C57B1/2J) were kept under controlled lighting (14 hr light, 10 hr dark) and temperature, with food and water ad libitum. When the animals reached a weight of 13–16 grams (which corresponds to the age of 20 to 22 days post partum), they were given a single injection (i.p.) of human menopausal gonadotropin (Humegon, Organon, The Netherlands) containing approximately 20 IU FSH and 20 IU LH (Ziebe et al. *Hum. Reprod.* 8, pp. 385–88 (1993)). 48 hours later the animals were killed by cervical dislocation.

Collection and cultivation of oocytes

The ovaries were removed, placed in HX-medium (se below) and freed of extraneous tissue. The collection- and culture medium consisted of Eagles minimum essential medium (Flow, USA), containing 4 mM hypoxanthine (HX), 3 mg/ml of bovine serum albumin, 0.23 mM sodium pyruvate, 2 mM glutamine, 100 U/ml of penicillin, and 100 μg/ml of streptomycin (all Sigma, USA). This medium is designated HX-medium. The same medium but without HX was used as control medium.

The influence of the test compounds on the meiosis of oocytes was studied in cumulus enclosed oocytes (CEO, Test A) and in denuded oocytes (DO, Test B). CEO were obtained by puncturing antral follicles of the ovaries under a dissecting microscope using a 27-gauge needle. Cumulus enclosed oocyte (CEO) of uniform size were selected and before use in Test A, they were rinsed three times in fresh HX-medium. Oocytes freed from cumulus cells, i.e. denuded oocytes, DO, for use in Test B were obtained by gently flushing CEO through a fine-bore mouth-controlled pipet. In Test A, CEO and in Test B, DO were cultured in 4-well multidishes (Nunclon, Denmark) in 0.5 ml of HX-medium containing the test compound at the concentration stated in the tables except the controls which were cultured in control medium. Each well contained 35 to 50 oocytes. The test cultures were made with different concentrations of the compounds to be tested as indicated in the tables.

The cultures were kept at 37° C. and 100% humidity with 5% $CO_2$ in the air for 24 hours.

Priming of oocytes, Test C(A) and C(B)

Test C(A) and C(B) was carried out as Test A and Test B, respectively, except that the oocytes were only kept in the medium containing the test compound for a period of time (priming period) ranging from 5 min to 3 hr at the beginning of the test. After the priming period, the oocytes were transferred to control medium and the cultivation was continued until 22 hours after the start of the test.

Examination of oocytes

By the end of the 24 hour culture period the number of oocytes with germinal vesicle (GV) or germinal vesicle breakdown (GVBD) and those with polar body (PB) was counted in an inverted microscope with differential interference contrast equipment. The percentage of oocytes with GVBD per total number of oocytes and the percentage of oocytes with PB per GVBD were calculated. The results for the Tests A, B, C(A) and C(B), calculated as units of MAS activity, are given in the tables in each of the examples. One MAS activity unit, MASU, is defined as:

$$\%GVBD_{control}/2$$

The number of MAS activity units, MASU, is calculated as:

$$2(\%GVBD_{test}-\%GVBD_{control})/\%GVBD_{control}$$

Example 1

Activation of meiosis in oocytes using cholestan-3β,5α,6β-triol.

Test A and Test B were performed as described above, using cholestan-3β,5α,6β-triol as test compound. The results are given in the table:

| Cholestan-3β,5α,6β-triol, μg/ml | No. of tests | Test A, MASU | Test B, MASU |
|---|---|---|---|
| 2.5 | 2 | 3.0 | 8.5 |
| 1.25 | 2 | 0.8 | 3.9 |
| 0.6 | 2 | 1.3 | 1.3 |

The cholestan-3β,5α,6β-triol used was obtained from Sigma (St. Louis, USA). It appears from the table that cholestan-3β,5α,6β-triol induces resumption of meiosis in oocytes in a dose-related manner.

Example 2

Activation of meiosis in oocytes using aminoguanidine hydrogencarbonate.

Test A and Test B were performed as described above, using aminoguanidine hydrogencarbonate as test compound. The results are given in the table:

| Aminoguanidine hydrogencarbonate, μg/ml | No. of tests | Test A, MASU | Test B, MASU |
|---|---|---|---|
| 2.5 | 2 | 3.7 | 2.8 |
| 1.25 | 2 | 2.5 | 2.4 |
| 0.6 | 2 | 2.0 | 0.6 |
| 0.3 | 2 | 0 | 0.6 |
| 0.15 | 2 | 1.2 | 0.8 |
| 0.08 | 2 | 2.1 | 1.6 |

The aminoguanidine hydrogencarbonate used was obtained from Aldrich Chemical Co., Inc. (Milwaukee, Wis.). It appears from the table that aminoguanidine hydrogencarbonate induces resumption of meiosis in oocytes in a dose-related manner.

Example 3

Activation of meiosis in oocytes using amphotericin B.

Test A and Test B were performed as described above, using amphotericin B as test compound. The results are given in the table:

| Amphotericin B, μg/ml | No. of tests | Test A, MASU | Test B, MASU |
|---|---|---|---|
| 1.25 | 3 | 5.9 | 5.9 |
| 0.6 | 2 | 1.3 | 3.7 |
| 0.3 | 1 | 2.5 | 0.8 |

The amphotericin B used was obtained from Bristol-Myers Squibb. It appears from the table that amphotericin B induces resumption of meiosis in oocytes in a dose-related manner.

Amphotericin is toxic at concentrations above 1.25 μg/ml. Concentrations up to 50 μg/nil have been tested.

Priming of oocytes with amphotericin B:

The results are shown in the table:

| Amphotericin B, μg/ml | No. of tests | Priming period | Test C(A), MASU | Test C(B), MASU |
|---|---|---|---|---|
| 1.25 | 2 | 5 min | 0.6 | 0.5 |
| 1.25 | 2 | 10 min | 0.7 | 1.4 |
| 1.25 | 2 | 30 min | 3.7 | 2.1 |
| 1.25 | 4 | 1 hr | 5.0 | 2.7 |
| 1.25 | 3 | 2 hr | 6.4 | 6.1 |
| 1.25 | 2 | 3 hr | 7.6 | 4.4 |

As it appears from the table, even an exposure to amphotericin B lasting only 5 minutes is sufficient to start resumption of meiosis in both DO and CEO.

Example 4

Activation of meiosis in male germ cells using amphotericin B.

The test system consisted of foetal mouse gonads, day 11.5 p.c. One gonad from each foetus was used as control and the other one as test gonad. The gonads which differentiated during the culture period were cultured for 6 days in a chemically defined culture medium under normal culture conditions, see Westergaard et al. *Fertil. Steril.* 41, p. 377 (1984). To the culture medium in which the test gonads were cultured varying amounts of Amphotericin B was added as indicated in the table. After the culture period, the control gonads only contained non-meiotic germ cells. A semi-quantitative account of the results with the test gonads obtained by microscopy after staining is given in the table below wherein indicates no response and "+", "++" and "+++" indicates increasing responses:

| Amphotericin B, μg/ml | Response |
|---|---|
| 10 | +++ |
| 5 | +++ |
| 1.25 | ++ |
| 0.5 | + |
| 0.1 | − |

The amphotericin B used was obtained from Bristol-Myers Squibb. As it appears from the table, amphotericin B activates meiosis in male germ cells in a dose-related manner.

We claim:

1. A method of stimulating the meiosis of a mammalian germ cell, comprising inhibiting an enzyme involved in the biosynthesis of cholesterol by administering an enzyme inhibitor compound resulting in stimulation of meiosis in said germ cell.

2. The method of claim 1, wherein the enzyme is selected from the group consisting of lanosterol 14 reductase, 4-demethylase, and lanosterol 8-7-isomerase.

3. The method according to claim 1, wherein the germ cell is a human germ cell.

4. The method according to claim 1, wherein the germ cell is an oocyte.

5. The method according to claim 1, wherein the germ cell is a male germ cell.

6. The method of claim 1, wherein said enzyme inhibition results in accumulation of an endogenous meiosis activating substance.

7. The method of claim 6, wherein the endogenous meiosis activating substance is 4,4-dimethyl-5α-cholesta-8,14,24-triene-3β-ol.

8. The method of claim 6, wherein the endogenous meiosis activating substance is 4β-methylzymosterol.

* * * * *